United States Patent [19]

Gallant

[11] Patent Number: 4,730,259

[45] Date of Patent: Mar. 8, 1988

[54] MATRIX CONTROLLED EXPERT SYSTEM PRODUCIBLE FROM EXAMPLES

[76] Inventor: Stephen I. Gallant, 14 Porter Rd., Cambridge, Mass. 02140

[21] Appl. No.: 707,458

[22] Filed: Mar. 1, 1985

[51] Int. Cl.$^4$ .............................................. G06F 15/18
[52] U.S. Cl. .................................... 364/513; 364/300; 364/415
[58] Field of Search ............... 364/513, 200 MS File, 364/900 MS File, 300 MS File, 413, 415; 340/146.2

[56] References Cited

U.S. PATENT DOCUMENTS

| | | | |
|---|---|---|---|
| 4,053,871 | 10/1977 | Vidalin et al. | 340/146.2 |
| 4,286,330 | 8/1981 | Isaacson | 364/900 |
| 4,290,114 | 9/1981 | Sinay | 364/900 |
| 4,315,309 | 2/1982 | Coli | 364/200 |
| 4,347,568 | 8/1982 | Giguere et al. | 364/300 |

OTHER PUBLICATIONS

Marvin Minsky and Seymour Papert, *Perceptrons, An Introduction to Computational Geometry*, pp. 161–167, 1969.
*Rule–Based Expert Systems*, Addison-Wesley, 1984, Chapter 9, B. Buchanon et al.
*Technical Report CMU-CS*-84-119, Carnegie-Mellon University, Department of Computer Science, May 1984, G. Hinton et al., "Boltzmann Machines: Constraint Satisfaction Networks That Learn".
*Proceedings with the National Academy of Sciences, United States*, 1982, 79, 2554–2558, "Neural Networks and Physical Systems with Emergent Collective Computational Abilities", J. Hopfield.
*Science*, "Expert Systems Research", Apr. 15, 1983, vol. 220, No. 4594, 261–268, R. Duda et al.
Schwartz, Tom "Software & The Law: The Battles are Coming" *Applied Artificial Intelligence Reporter*, Dec. 1986, pp. 8–9.

*Primary Examiner*—Gary V. Harkcom
*Attorney, Agent, or Firm*—Robert M. Asher

[57] ABSTRACT

An expert system in which an inference engine is controlled by a matrix of learning coefficients and a method for generating a matrix controlled expert system from examples. The inference engine determines likely values and final determinations for resultant variables in the matrix, the variables being representative of responses or actions. The inference engine also determines an input variable which will contribute to making a final determination of a resultant variable. The matrix may be generated by training examples and/or rules and it may be modified dynamically by additional examples as the system operates.

36 Claims, 11 Drawing Figures

MATRIX CONTROLLED EXPERT SYSTEM PRODUCIBLE FROM EXAMPLES

BACKGROUND OF THE INVENTION

This invention relates to expert systems. An expert system is a computer programmed to exhibit human expert-like ability for solving problems and generally containing an external interface which interacts with an inference engine responsive to a rule base. The inference engine responds to data supplied by the external interface in accordance with rules set out in its rule base. Expert systems have been developed for a number of applications including giving medical advice, configuring computer or other electronic hardware, analyzing geological data, and warning of malfunctions in an industrial plant.

The external interface is a problem specific piece of computer software which receives input from an external interactive terminal or from measurement devices and outputs queries or commands to the external terminal or signals to operate actuators, alarms, displays, etc. The programming of such an interface is well known to those skilled in the art.

An inference engine is a computer program that uses a base of knowledge or rules to make inferences from input information until an appropriate response can be deduced. When additional information is needed to provide a final response, it requests the information through the external interface. It is usually possible to reproduce and use the same inference engine in a number of different expert system applications with no more than a slight modification.

The knowledge or rule base is a set of rules that govern the behavior of the inference engine and hence the entire system. Typically, each rule has the following structure:

IF <Condition 1> and <Condition 2> and . . . <Condition M>
THEN <Action 1> <Action 2>... <Action N>.

There may be several rules which produce the same set of actions.

Examples of conditions, from a fictional medical application used herein for descriptive purposes, include "high white cell count", "allergic to cacamycin", and "overweight". Examples of actions include "administer cacamycin" and "administer merdecillin". The interpretation of a rule is that if all of the conditions hold then all of the actions are executed. The actions are effectuated through the external interface. The responses may be as simple as driving the display or may involve triggering some actuator in the industrial plant such as opening a safety valve.

Some actions are also considered conditions for other rules. For example, the action "administer cacamycin" may correspond to a condition for a rule of the form IF <administer cacamycin> THEN <Do Not administer merdecillin>. This rule implies that it would not be prope to administer merdecillin if cacamycin is being administered. Such actions need not affect the external environment directly; their primary use may be as conditions for other rules.

In the prior art, rules are generally constructed for an expert system by either having a human expert provide the rules in a form suitable for the rule base or by having another person generally known as a knowledge engineer convert the information from an xpert into appropriate rules. It is often the case that a human expert in a particular area has difficulty formulating his or her knowledge as a set of rules. The process of generating and perfecting a set of rules has been universally recognized as the most time consuming, difficult, and expensive process involved in building an expert system. It is frequently difficult to reduce expertise to a set of rules.

Various approaches have been tried to ameliorate the problem of generating rules for a expert system. One approach is to create a "user friendly" interface to ease the human task of adding new rules as described in Buchanon, B. and Shortliffe, *Rule-Based Expert Systems,* Addison Wesley, 1984, Chapter 9. Another system which has been made available is contained within the software product "Expert-Ease" manufactured by Export Software International Limited. This product apparently takes training examples input into the system and builds a decision tree based on these examples using statistical methods. This tree can then be coupled with a decision tree controlled inference engine to produce an expert system.

A decision tree controlled expert system has the shortcoming of being overly sensitive to noisy data. The deviation in a variable's value may take the inference engine through a branch of the decision tree from which it cannot reach the correct answer unless the tree is made very large.

Moreover, there is no provision for insuring that data which is close to a training example will result in the training example's correct response.

SUMMARY OF THE INVENTION

The present invention is a general purpose matrix controlled expert system. The expert system includes a matrix of learning coefficients, an external interface and inference engine. The knowledge base of the expert system of the present invention is stored in the form of the matrix of learning coefficients. The external interface receives input information and provides the output responses of the system. The inference engine produces responses to input data in accordance with the matrix of learning coefficients. The inference engine attempts to determine the value of goal variables. A goal variable corresponds to an action or response to be provided by the expert system through the external interface. When the goal variables cannot be sufficiently determined, the inference engine determines a piece of input information that would be useful in determining a response or action to be taken and cause the external interface to request the information.

In accordance with the method of the present invention, the matrix of learning coefficients can be generated from examples including values for a plurality of conditions with corresponding values for the desired responses or actions. Rules may also be input but advantageously this is not necessary. This approach greatly simplifies the task of generating an expert system since it is no longer required that an expert develop the rules which support the system.

The expert system of the present invention is also much easier to debug or perfect. A set of training examples can be used to generate the expert system. If the system fails to provide the correct response for some set of inputs, these inputs with the correct response can be used to provide an improved system. In accordance with the preferred embodiment of the present invention the expert system can dynamically improve its matrix by continuously updating its matrix as new examples are input through the external interface.

The expert system of the present invention has the advantage of being "softer" than a decision tree based system. It is soft in the sense that inputs that are close to a particular training example are more likely to be handled the same as that training example. This enables improved performance in noisy environments.

A further advantage of the expert system of the present invention is that it is well suited to parallel implementation in hardware.

A still further advantage of the expert system of the present invention is that it tends to be only weakly affected by an error in an individual coefficient in the matrix of learning coefficients. This makes hardware implementations more error resistant.

A still further advantage of the expert system of the present invention is that at every step the system has readily available a best guess of values for output responses and intermediate decisions.

A still further advantage of the expert system of the present invention is that it provides for a very fast operation when used.

Other objects and advantages of the invention will become apparent during the following description of the presently preferred embodiments of the invention taken in conjunction with the drawings.

BRIEF DESCRIPTION OF THE DRAWINGS

FIG. 6b is a flow chart of the routine ROWCHECK called by the learning method of FIG. 6a.

DETAILED DESCRIPTION OF THE PREFERRED EMBODIMENTS

Figure 1:
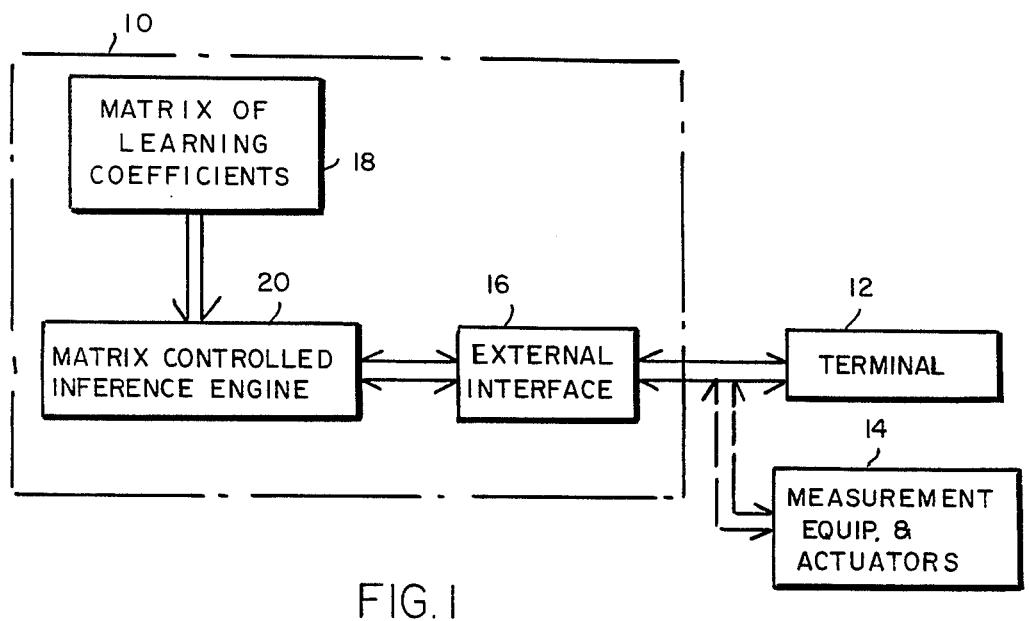
FIG. 1 is a schematic diagram of an expert system of the present invention.

Referring now to FIG. 1, an expert system 10 of the present invention is shown. The expert system 10 communicates with users through a terminal 12. The expert system 10 is a program embedded in a general purpose computer of known type. In addition to or in replacement of the terminal 12, the expert system 10 may be connected to measuring devices and actuators 14 so that the expert system may control a system such as a heating or cooling system, a burner control system, a communications system, etc.

The expert system 10 communicates with the terminal 12 and/or the measurement equipment and actuators 14 through an external interface 16. The external interface 16 facilitates the interaction with the user of the system. The external interface 16 may be programmed by well known methods. The interface outputs information generated by the expert system to the terminal 12 or the measurement equipment and actuators 14. For instance, it would cause messages to be displayed on the terminal or may cause actuators to be activated. Interface 16 also provides prompts to the terminal 12 to get a user to input the appropriate information into the expert system 10.

The performance of the expert system 10 is dependent upon a matrix controlled inference engine 20. A matrix of learning coefficients 18 provides the knowledge base from which the inference engine 20 makes its inferences and deductions. A matrix of learning coefficients may be generated by known learning methods. There are a number of different learning methods that may be utilized to produce a matrix of learning coefficients 18, including perceptron learning disclosed in Minsky, M. and Papert, S. *Perceptrons: An Introduction to Computational Geometry*, MIT Press, Cambridge, Mass. (1969); Boltzmann Machine Learning disclosed in Hinton, G. E., Sejnowski, T. J. and Ackley, D. H., "Boltzmann Machines: Constraint Satisfaction Networks that Learn," *Technical Report CMU-CS*-84-119, Carnegie Mellon University, Department of Computer Science; Hopfield's Method disclosed in Hopfield, J. J., "Neural Networks and Physical Systems with Emergent Collective Computational Abilities," *Proceedings with the National Academy of Sciences*, U.S., 1982, 79, 2554–2558; and others. In addition, a learning algorithm of the present invention is disclosed herein with reference to FIGS. 6a–d.

To assist in clarifying the definition and operation of a matrix of learning coefficients, an example will be described. The example used herein is a fictional medical application, however the operation of the present invention may extend to a wide variety of other systems. A matrix of learning coefficients 18 for the example is diagrammatically shown in FIG. 2. The expert system of the present invention represents the conditions, responses and actions of any particular application as a number of different types of variables. Variables which are only used as conditions are input variables 28. The input variables may only be given a value by some external source via the external interface such as being entered through a keyboard or via a reading taken from some measuring device. The expert system does not attempt to deduce the value of input variables. The object of the expert system is to determine the responses or actions which are represented as goal variables 32. Variables whose value may be input through the expert system or determined by the expert system but which are not goal variables 32 are called intermediate variables 30 herein.

A matrix of learning coefficients 18, as the term is used herein, provides an arithmetic representation for each condition, response or action which enters or leaves the expert system. The matrix includes primary variables 22 represented by X1, X2, X3, X4, X5, X6, X7, X8, X9 and resultant variables 24 represented by Y1, Y2, Y3, Y4. The primary variables 22 represent conditions and the resultant variables represent the responses, actions, or intermediate determinations. In the embodiment shown, each primary variable 22 is given a column in the matrix and each resultant variable 24 is given a horizontal row. The matrix may be more efficiently stored as a set of lists rather than as a matrix, yet still retain its identity as a matrix of learning coefficients. It is obviously irrelevant whether the primary variables 22 are switched with the resultant variables 24 with respect to occupying either the columns or the rows of the matrix 18. The primary variables 22 may include input variables, intermediate variables and goal variables. The primary variables define the conditions upon which the resultant variables 24 depend. The resultant variables 24 include intermediate variables and goal variables. A resultant variable 24 may also be a primary variable, since some responses, actions or intermediate determinations may be conditions for other responses, actions, or intermediate determinations. In addition to the primary variables 22 a column is also provided for constants 26. The value of a resultant variable is determined by knowing the value of the primary variables on which it depends and the matrix values assigned to those primary variables and the constant for that resultant variable.

In the fictional medical example, the input variables 28 include such facts as whether or not there is a fever between 100° and 102° F., patient is overweight, has a high white cell count, tough skin, red rash and allergic to cacamycin. From among these input facts one may determine such intermediate variables 30 as whether the patient has an inflamed plethorus or poblanocosis. The goals of the expert system 10 of the example is to determine whether cacamycin should be administered and whether merdecillin should be administered. The values of these variables may take on the values true, false or unknown. In the preferred embodiment of the present invention the value 1 is assigned to a variable which is true, minus 1 is assigned to false and 0 is assigned to unknown. It would be possible within the scope of the present invention to assign probabilities of truth or falseness to the variables such that it would be possible to indicate a patient is slightly overweight or has a moderately high white cell count as opposed to merely indicating true or false. Likewise, someone making inputs into this system might be able to indicate a probability that the patient has poblanocosis which may be taken into account by the inference engine. The embodiment described herein assigns the values of 1, 0 or −1 to variables, however it would also be possible to assign a likelihood to each variable consisting of an integer value between 5 and −5 for instance. It is additionally possible to assign fractional values to the variables. The presently preferred embodiment limits the values of the variables to −1, 0 or 1.

One of the advantages of using the matrix of learning coefficients in the expert system 10 of the present invention is that the matrix 18 may be generated from training examples. It is not necessary for an expert to provide rules to the expert system 10 to make it knowledgeable. It is, however, helpful to have an expert provide dependency lists for the intermediate and goal variables 24. By limiting the matrix value for each resultant variable 24 to including only values for those primary variables 22 upon which a resultant variable 24 depends, a more refined and accurate matrix will be more quickly arrived at by a learning method. The constant 26 is on the dependency list for all resultant variables 24. In the fictional medical example, we have assumed that the following training examples have been provided:

| Example No. | 1 | 2 | 3 | 4 | 5 | 6 | 7 | 8 |
|---|---|---|---|---|---|---|---|---|
| Fever Between 100 & 102 | T | F | F | T | T | T | T | F |
| Overweight | T | F | F | T | F | F | T | T |
| High White Cell Count | T | F | T | F | F | F | T | T |
| Toughening of Skin | F | T | T | F | T | T | F | F |
| Red Rash on Skin | F | T | F | T | T | T | F | T |
| Allergic to Cacamycin | F | F | T | F | T | F | T | T |
| Inflamed Plethorus | T | F | T | F | T | T | T | F |

| Example No. | 1 | 2 | 3 | 4 | 5 | 6 | 7 | 8 |
|---|---|---|---|---|---|---|---|---|
| Poblanocosis | F | T | T | F | T | T | F | T |
| Administer Merdecillin | F | F | T | F | T | F | T | T |
| Administer Cacamycin | T | T | F | F | F | T | F | F |

It is also helpful to provide dependency information such as the following:

Inflamed plethorus only depends on fever, weight and white cell count.

Poblanocosis only depends on white cell count, tough skin and red rash.

Administering merdecillin only depends on inflamed pletorus, poblanocosis and administering cocamycin.

Administering cocamycin only depends on inflamed plethorus, poblanocosis and allergy to cocamycin.

The matrix could be generated solely by rules provided by an expert, however, as has already been discussed, the determination of appropriate rules by an expert is a highly difficult task. However, there often are a number of rules which are easily known and which can be input into the determination of the learning matrix in addition to the training examples. For the embodiment described herein, a rule can be represented in the following manner:

$$<X6, X7, X8> = <1, \#, \#> \text{ implies } Y4 = -1$$

A rule for a resultant variable is given by providing a value of +1, −1 or # for primary variables on the dependancy list of the resultant variable. A value of 1 signifies true, −1 signifies false and # signifies irrelevant. For example the rule provided above indicates that "If the patient is allergic to cacamycin, then do not administer cacamycin." Knowing the matrix form for rules allows the construction of a "rule compiler" to transform rules expressed in an easy to read form into the matrix form. A rule compiler can transform a rule written with logical OR's into the accepted format which in the present embodiment uses only logical AND's. This may produce more than one rule for each rule which is input and may create additional intermediate variables. To illustrate this process, suppose Y1 depends on X1, X2 and X3 and a rule is desired which states:

If X1 and NOT (X2 or X3) then Y1 is false. Then the rule compiler can create an intermediate variable I dependent on X2 and X3 along with rules:

$$<X2, X3> = <1, \#> \text{ implies } I = 1$$

$$<X2, X3> = <\#, 1> \text{ implies } I = 1$$

I is added to the dependency list for Y1 and the following rule is included among the rules for Y1:

$$<X1, X2, X3, I> = <1, \#, \#, -1> \text{ implies}$$
$Y1 = -1$. The construction of a rule compiler may be accomplished by well known methods familiar to those skilled in the art.

Figure 2:
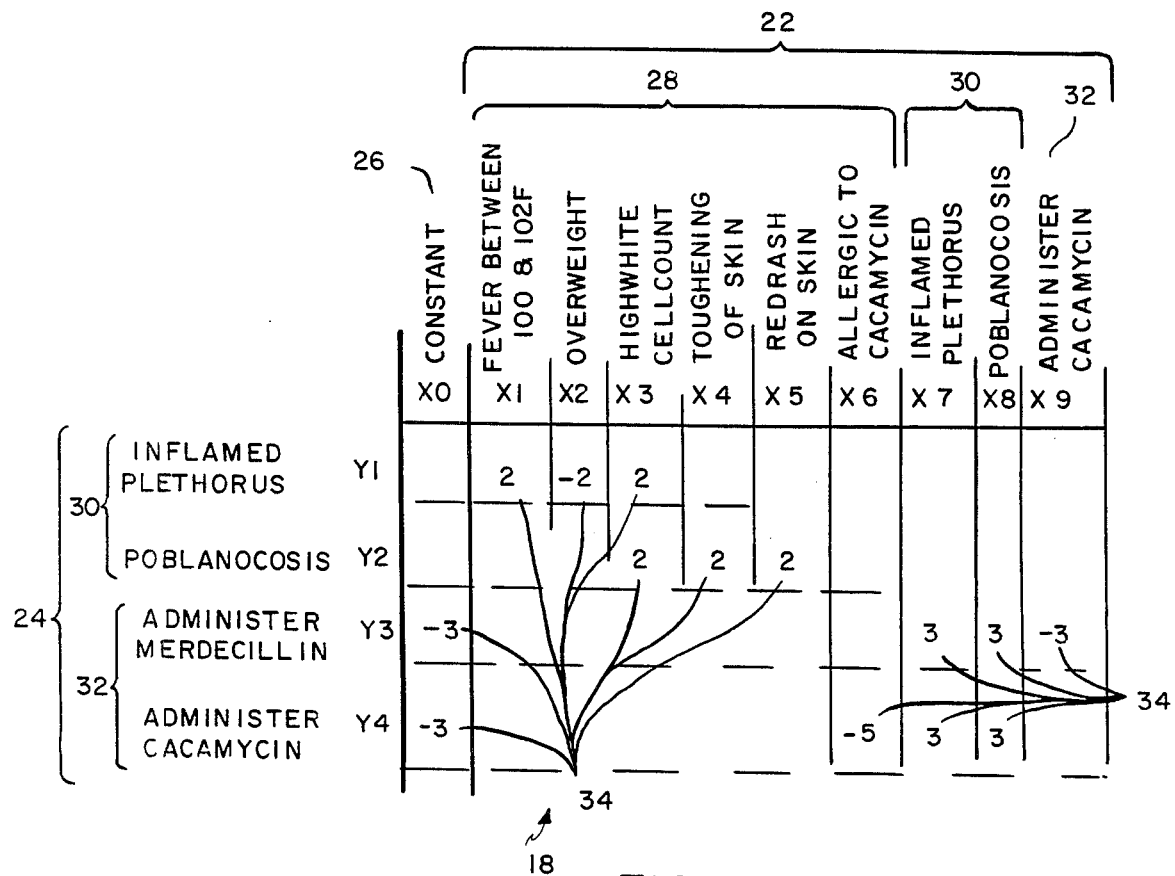
FIG. 2 is an example of the matrix of learning coefficients of FIG. 1.
Figure 3:
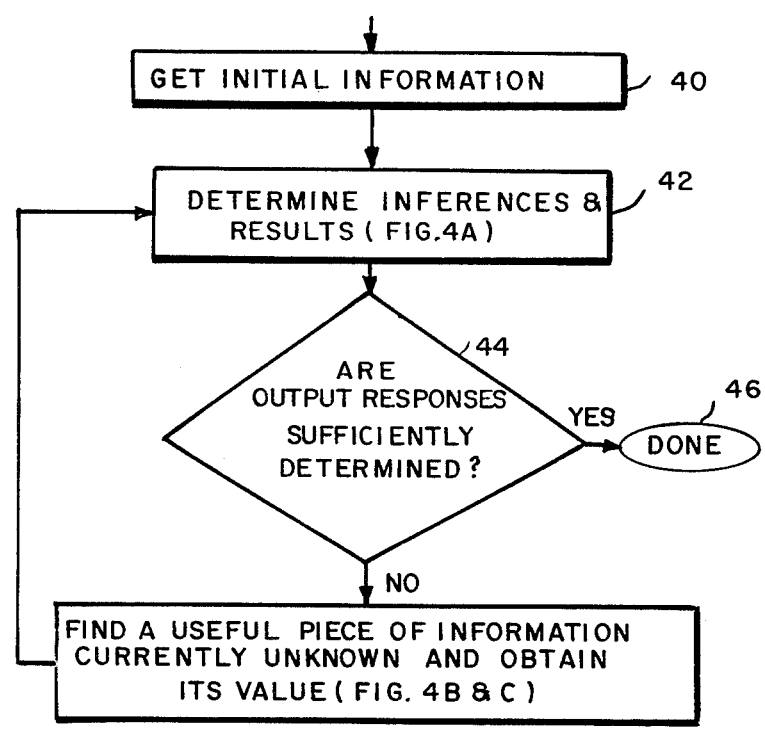
FIG. 3 is a flow chart of the matrix controlled inference engine of the present invention.

Using the dependency lists and training examples provided above for the fictional medical example a matrix of learning coefficients is produced which may be represented as the one shown in FIG. 2.

Each resultant variable 24 in the matrix has associated with it a vector which includes all of the matrix values for the primary variables which are in its dependency list and also includes a constant. The vector appears as a row of numbers in the learning matrix of FIG. 2. Primary variables which are not on the dependency list of the resultant variable are given the matrix value 0 in the respective row. Non-zero matrix values 34 are illustrated in the figure.

The matrix of learning coefficients of the present invention has the property that when a training example expressed in its corresponding integer form is multiplied by the respective matrix values in any row of the matrix, then the sum of the products resulting therefrom added to the constant term will have a result which is greater than 0 if the corresponding resultant variable is true or less than 0 if the corresponding resultant variable is false. Thus, if we look at example 3 and row Y 1, we compute:

$$(0)+(2)(-1)+(-2)(-1)+(2)(1)+(0)(1)+(0)$$
$$(-1)+(0)(1)+(0)(1)+(0)(1)+(0)(-1)=2$$

Since 2 is greater than 0, the value for Y1 (inflamed plethorus) is true.

Taking example 2 and row Y3, we compute:

$$(-3)+(0)(-1)+(0)(-1)+(0)(-1)+(0)(1)+(0)$$
$$(1)+(0)(-1)+(3)(-1)+(3)(1)+(-5)(1)=-8$$

Since −8 is less than 0, the value for Y3 (administer merdecillin) is false as desired by the example.

In complex problems it may not always be possible to construct a matrix which satisfies the relationships for all of the training examples. If this should occur during the generation of the matrix, the learning method disclosed below converges upon a matrix which satisfies as many relationships as possible.

The matrix controlled inference engine 20 of FIG. 1 has the task of deducing the responses or actions to take considering partial or total input information. The matrix of learning coefficients 18 is used to arrive a the appropriate responses or actions. If total information is provided, the values of all of the resultant variables 24 will usually be readily determinable. If only some of the input variables 28 are known, then there may be some resultant variables 24 which cannot be determined for a certainty. Since the present invention is numerically based, a probability or likelihood value can be determined for the resultant variables which aren't yet assured. The inference engine 20 is also responsible for determining from among the missing input variables 28, a variable which would be valuable in reaching a final determination as to the value of one of the goal variables 32. The methods used by the present invention for performing the functions of the matrix controlled inference engine 20 are illustrated in FIGS. 3, 4a, 4b and 4c.

By providing a matrix 18 which controls the functioning of the inference engine 20 in the present invention, the determination of results is advantageously affected by feedback. In other words, after taking one pass through the matrix and attempting to determine the values of the resultant variables 24 there may be some which have not been determined. A value cannot be determined for a certainty if the matrix values of the unknown variables are large enough to change the sign of the final result computed for the known variables. However, there may be some resultant variables 24 which have been determined either from partial or total information in their dependency lists which may be used to help come to a final determination of other resultant variables 24. As previously stated, a resultant variable 24 may also be a primary variable 22. Upon determining the value of a resultant variable 24, this additional information may be used in the next pass through the matrix 18 in determining other values for resultant variables 24. The feedback allows for more efficient storage of an accurate system than a tree driven system, for instance. In a tree driven system successive deductions move down the tree and there is rarely any way to get from one branch to another. Thus, to achieve great accuracy each branch might have a huge number of subbranches in a tree driven system. Thus, the storage requirements could be immense. In a restricted finite memory, operating a tree driven system it is possible for an example which varies slightly from a training example to get carried away down the wrong branch of the tree. Whereas, with the matrix controlled system an example which is only slightly different from a training example will more likely produce a result similar to that of the training example.

Another major advantage of the matrix controlled inference engine 20 is that resultant variables 24 may be determined even though all of the variables on the dependency list have not been provided. If the unknown variables have matrix values 34 for a resultant variable 24 which are sufficiently low so that no matter what the actual value of the variable is the sign of the sum already obtained with the partial information will be unchanged, then the resultant variable 24 has been determined for certainty. For example, if in the example of FIG. 2, if it is known that the patient does have a fever between 100 and 102 F. and is not overweight, then we can compute for Y1 (inflamed plethorus): $(2)(1)+(-2)(-1)=4$. High white cell count is unknown and the other primary variables are zero in the matrix and thus do not figure in the computation. Since the matrix value 34 of high white cell count is 2, regardless of whether high white cell count is true or false, the result which is now +4 will still be positive. Thus, we have determined for a certainty that inflamed plethorus is true with only partial input information. If it is possible that the value of the resultant variable 24 may be changed depending upon the unknown information then the matrix controlled inference engine 20 will make a selection of an input variable that will be useful in arriving at a final determination.

Referring now to FIGS. 3, 4a, 4b and 4c the operation of the matrix controlled inference engine can be seen in greater detail. Information is input into the system and received by the inference engine 20 through the external interface 16 in block 40. Unknown variables are initially set to 0. The value of the variable is identified as t herein. Thus initially t equals 0 for all variatbles. t is also defined for the constant (J=0) term and this value of t is fixed at 1. This simplifies computations by allowing the constant to be treated as a variable whose value has been determined. Input information will set the t values of the other variables at +1 if true and −1 if false in the presently described embodiment. In the present embodiment, each variable is also given a value for a likelihood L. The likelihood of a variable will be between −1 and +1 and will generally indicate a guess as to the value of unknown variables. The size of the likelihood will indicate a rough approximation of the confidence which the system has in the guess. The likelihood is initially set at 0. For known values, the known likelihood L is equal to t. After all of the available initial information has been received by the inference engine, in block 42, the inference engine 20 determines the values t of any resultant variables 24 that can be determined from the initially provided information. This process will be described in greater detail with respect to FIG. 4a.

Next, the inference engine 20 determines whether it has sufficiently determined the values of goal variables 32 in block 44. This determination may be adjusted to suit the user of a system. In some systems, it may be sufficient to have determined the value of any goal variable 32. However, there may also be systems in which it is desirable to verify the results of as many goal variables 32 as possible, in other words reaching the point where there is no longer any further information which would affect the values of the goal variables 32. If responses have been sufficiently determined, then the inference engine 20 is completed with its work as indicated in block 46. If more information would be helpful, the inference engine 20 proceeds to block 48 where it determines a useful piece of information, requests that information through the external interface and receives an answer. This sequence is described in greater detail with reference to FIGS. 4b and 4c. After receiving the new additional information, the inference engine 20 repeats its cycle by returning to block 42 where once again it attempts to determine what the values are of the resultant variables 24.

Figure 4A:
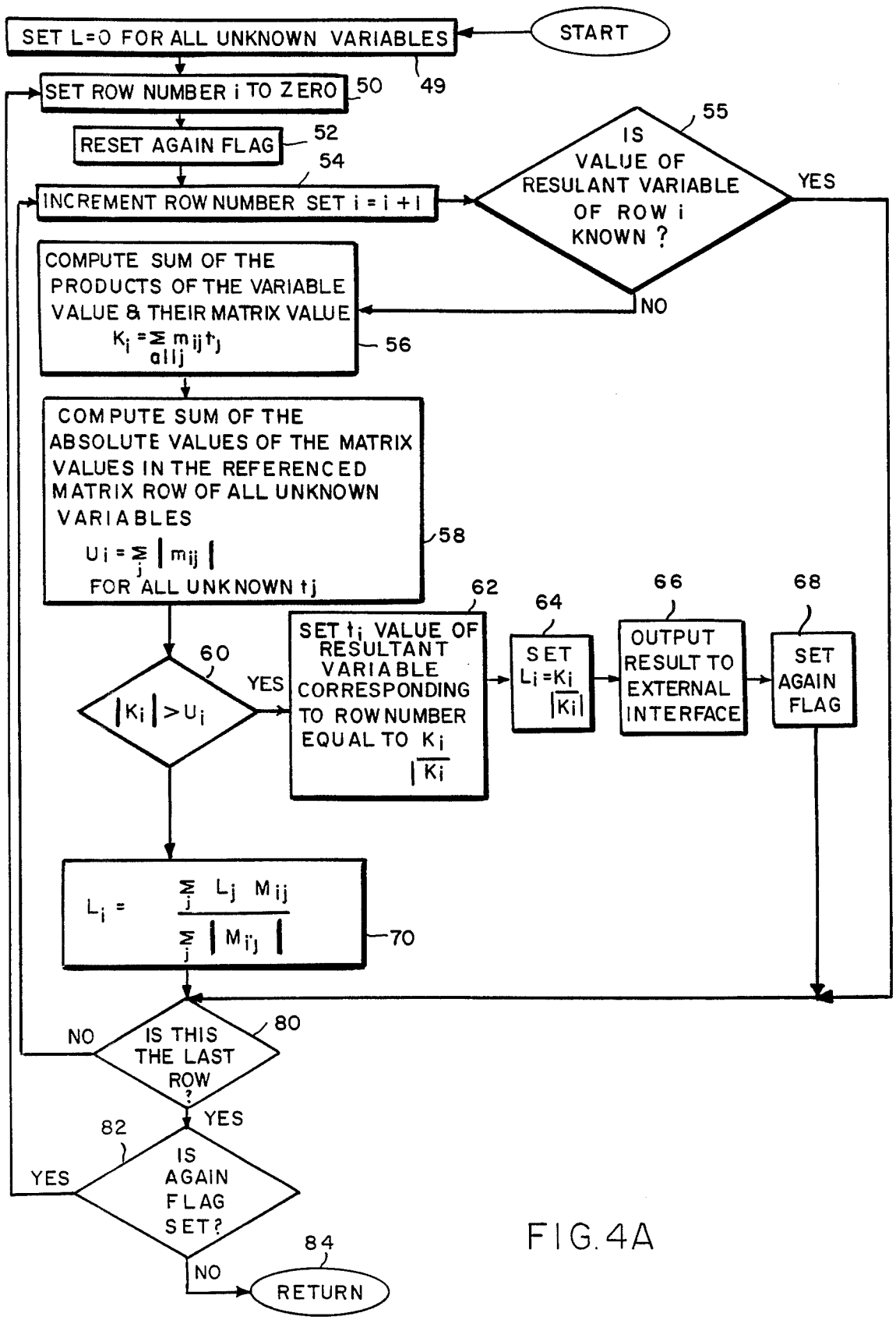
FIG. 4a, b and c are flow charts of selected portions of the matrix controlled inference engine of FIG. 3.

Referring now to FIG. 4a, a flow chart for the determination procedure described in block 42 is shown. The heuristic of FIG. 4a is only one of the possible heuristics which may be selected for use in the inference engine 20 for this purpose.

In block 49 the likelihood, L, for all unknown variables is initialized to 0. It would also be possible to specify expected likelihoods not equal to 0 for some or all variables to aid in determining which goal variable and/or question is to be pursued. For example, a physician suspecting poblanocosis might specify that the corresponding likelihood be greater than or equal to 0.75. This would be treated as a minimum value for the corresponding L computation in block 70 and could result in poblanocosis related treatments being explored sooner. In block 50, the inference engine 20 begins by setting i equal to zero. The variable i is used to index through the resultant variables 24. Each resultant variable 24 has a row associated with it in the matrix of learning coefficients 18. In block 52, a flag identified as the "again flag" is reset. As will be seen later in this description, the "again flag" permits the operation of the feedback feature of the matrix controlled inference engine. In block 54, the row number is incremented by 1.

The matrix of learning coefficients 18 assigns a matrix value 34 to each primary variable 22 which is on the dependency list of each resultant variable 24. Primary variables not on the dependency list for a resultant variable 24 have a matrix value equal to zero. The matrix value 34 is indicated as "m" in the flow chart. In block 56, the inference engine 20 computes the sum of the products of the matrix value times the known value t for each primary variable across the matrix row. The letter "j" indexes the primary variable and the constant. The constant is assigned j=0. The resulting sum, indicated as "K", will be used to determine whether the value of the resultant variable 24 has been sufficiently determined. Variables whose value is unknown have no effect on the value of "k" since unknown variables have a t equal to 0. In the flow chart "i" is used to indicate the row number in the matrix and "j" is used to indicate the column number in the matrix. K is computed across all of the columns j.

In block 58, a sum of the absolute values of the matrix values 34 is computed for all of the variables whose value t is unknown (i.e. equal to 0). The sum of the absolute values of the matrix values is referred to as "U" herein. In block 60, the inference engine compares the absolute value of K with the value U. If the absolute value of K is greater than U, then regardless of what the values are of the unknown primary variables the final determination of the resultant variable's value will be unchanged. The resultant variable's value is set equal to +1 if K is positive over the entire row and is equal to −1 if K is negative over the entire row, in block 62. The likely value L for the resultant variable is set to the same resultant in block 64. Since U is smaller than the absolute value of K, the values of the remaining unknown variables are irrelevant to the final determination and the finally determined value of the resultant variable can be used to output the appropriate response or action through the external interface 16. Then, in block 68 the again flag is set. The again flag will cause the inference engine 20 to take another pass through all of the rows and make another attempt at determining the values of the resultant variables since the value of the resultant variable being presently computed has been determined. If this resultant variable is also a primary variable, it may affect other resultant variables and this additional information may aid in arriving at further final determinations of values for resultant variables.

If the matrix values 34 of the unknown variables are sufficiently high so that the resultant variable 24 cannot be finally determined, then a likelihood value L will be determined. In block 70, the likelihood value of the resultant variable is computed as the sum of the elements in row i multiplied by corresponding likelihoods divided by the sum of the absolute values of all elements in row i. The sign of the likelihood indicates the likely value for the resultant variable 24. The size of the likelihood gives a rough approximation of the confidence that the system has in its guess as to the actual value of the resultant variable.

Upon completing the computation of the likelihood of the resultant variable 24, the inference engine 20 determines whether this is the last row in its matrix of learning coefficients. If it is not the last row, there are more computations to be made and the inference engine 20 returns to block 54 where it begins its computation of the values for the next resultant variable. If this is the last row of the matrix, then a first pass through the matrix has been completed. If none of the resultant variables have been finally determined, then there is no additional information and this inference engine task is completed. However, if a resultant variable has been determined, then the again flag will have been set and the inference engine will return to the top of the matrix to recompute the resultant variable values using the newly computed information in addition to the input information that was already received.

Figure 4B:
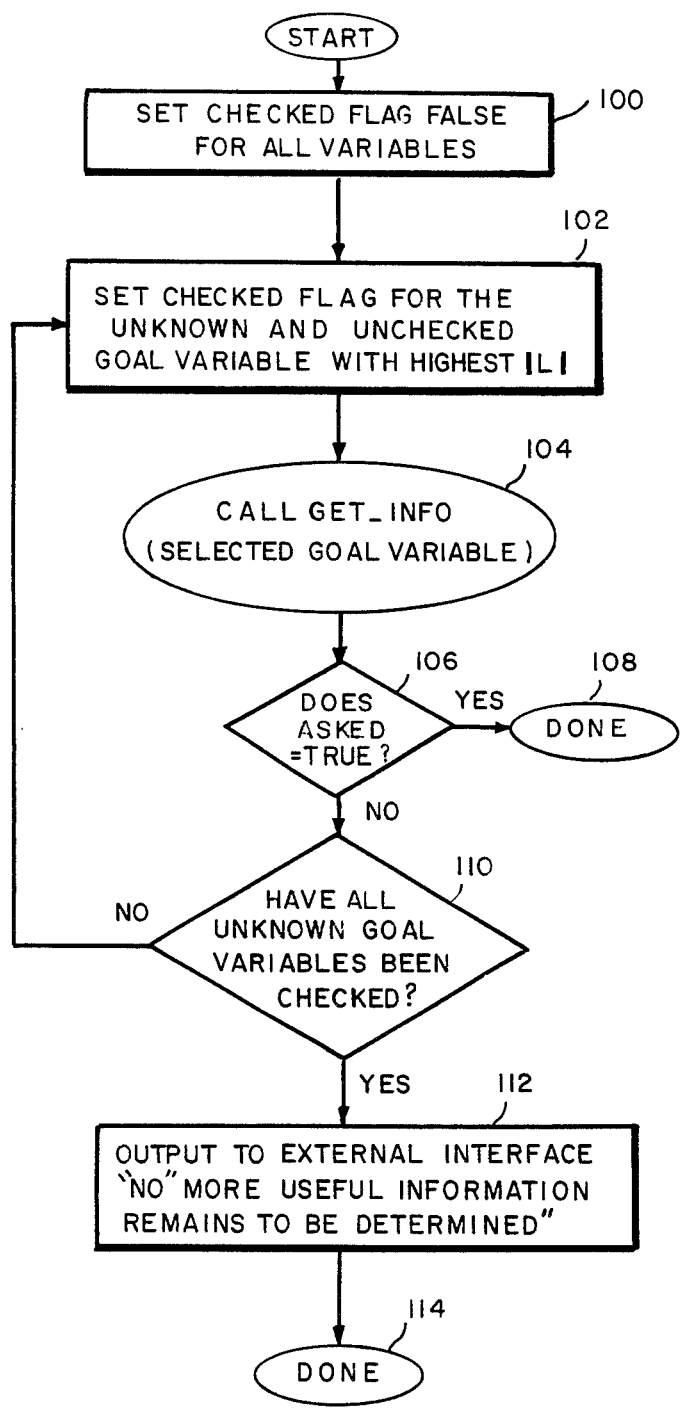

Referring now to FIG. 4b, another major task of the inference engine 20 is to determine what would be a useful piece of information in arriving at a final determination of the value of a goal variable 32. The process begins by entering block 100 in which a "checked" flag is set to false for all variables. This helps the system keep track of which variables have been checked for determining the next input information to ask for. In block 102, the system sets the checked flag to true for the goal variable 32 which has the highest value for the absolute value of its likelihood, since it is generally expected that the higher the absolute value of the likelihood the closer the system is to making a final determination as to the value of that goal variable. The subroutine GET-INFO, is called for the goal variable selected.

Other heuristics are of course possible in block 102, such as using the highest likelihood rather than the highest absolute likelihood rather than the highest absolute likelihood to select a goal variable most likely to be true.

Figure 4C:
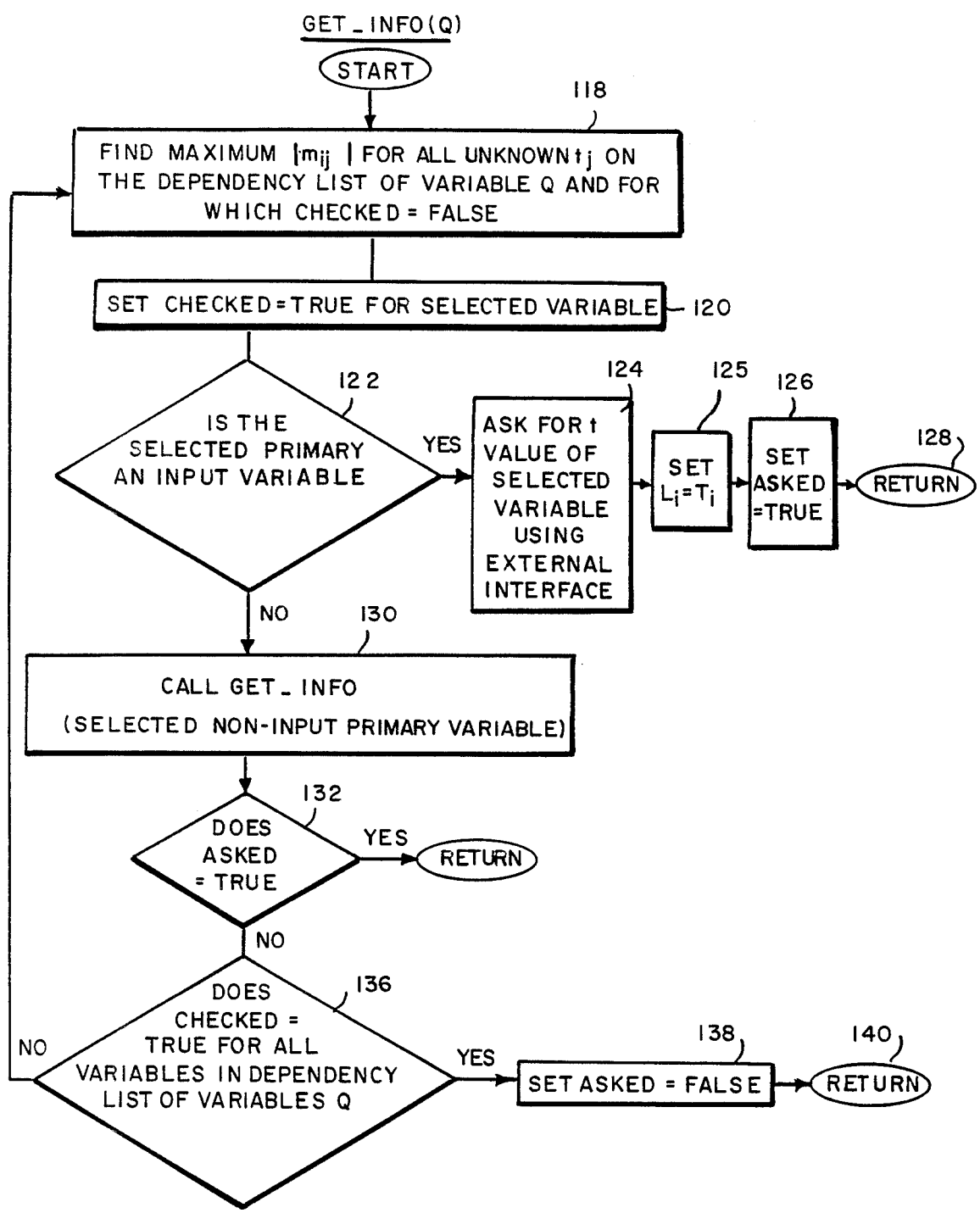

Referring now to FIG. 4c the subroutine GET-INFO is illustrated. The subroutine was called for the selected goal variable from FIG. 4b. In FIG. 4c, the selected variable which caused GET-INFO to be called is identified as Q. The dependency list includes all variables whose matrix value is non-zero in the row of the selected resultant variable. In block 118, the row for resultant variables Q is searched. In that row, all of the matrix values of variables whose t value is unknown and for which checked is false are looked at. The variable with the maximum absolute matrix value 34 is selected. Other heuristics are possible, such as choosing the variable with the maximum absolute value of the product of its likelihood and matrix value. In block 120, checked is set to true for the selected primary variable. Then in block 122, the program determines whether the selected primary variable is an input variable 28. If it is an input variable 28, the inference engine 20 will ask for the t value of that input variable by using the external interface, in block 124. This t value is copied to the corresponding likelihood in 125. In block 126, the asked flag is set to true. Then the routine is completed and control passes back to the point where the routine was called from as commanded in block 128.

If the selected primary variable was not an input variable 28, then in block 130 GET-INFO is recursively called for the selected non-input primary variable. In this situation, the inference engine 20 has determined that the variable which is likely to have an effect on the goal variable 32 which has almost been determined is a resultant variable 24. Thus, the program will attempt to find the input variable 28 which is most likely to give a determination of the value of the resultant variable 24 so that the resultant can be fed into the determination of the original goal variable 32.

After returning from the recursive call to GET-INFO, the program determines whether the asked flag is true in block 132. If asked is true that means that the external interface has requested further information and the GET-INFO routine is complete, thus control may be returned to the point of the call to GET-INFO as indicated by block 134. If GET-INFO was unsuccessful at determining an input variable 28 whose value should be asked for then in block 136 the program checks on whether checked is true for all variables in the dependency list of the row for Q, the resultant variable for which GET-INFO was called. If all of these variables have been checked then in block 138, asked is set to false and control is returned by block 140 to the point from which the routine GET-INFO was called. However, if some unchecked variables remained in the dependency list of the resultant variable, then the remaining variable with the maximum matrix value will be investigated as a likely candidate in identifying the next piece of useful information to be asked for.

Returning now to FIG. 4b, if GET-INFO was successful then block 106 determines that asked=true and that this task of the inference engine has been completed. The inference engine 20 may return to once again attempting to determine the values of the resultant variables. If "asked" is not true then the program looks in block 110 to see if all of the goal variables 32 have been checked. If not, the goal variable with the next highest absolute value of likelihood will be investigated by the routine GET-INFO to determine a useful piece of input information to inquire after. If all of the goal variables 32 have been checked and not a single input variable 28 was found to be of any value in making further determinations of the goal variables 32, block 112 causes the system to output the message that "No more useful information remains to be determined". At this point, the system may provide the terminal with the likelihood values of the goal variables 32 so that at least a best guess of the solutions is provided.

Other methods may be used and factors considered in determining the next input variable to ask about. In an alternative embodiment, each input variable can have a cost associated with it. The cost would approximate how costly or how difficult it would be to look for the value of the particular input variable. One alternate method of picking the next variable to ask about is to pick the one with the least cost. Another method is to use ratio of likelihood to cost to determine which goal variable should be looked at to find a good input variable to ask for. The cost of a resultant variable is the sum of the costs of obtaining the minimum amount of input information to get a final value determination. The dependency list can be looked at to find the lowest cost unknown input variable or the input variable with the highest absolute value for its matrix variable as performed in the presently preferred method.

Figure 5:
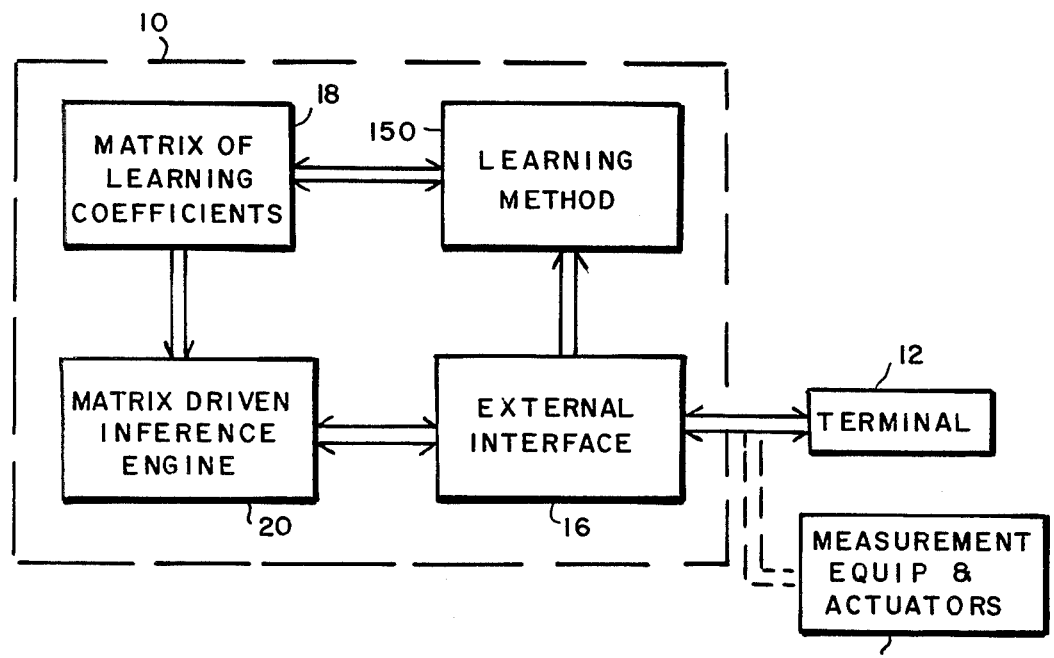
FIG. 5 illustrates a second embodiment of the expert system of the present invention.

Referring now to FIG. 5, a second preferred embodiment of the present invention is illustrated. In addition to the pieces of the expert system described above, the second embodiment includes a learning method 150. A learning method 150 generates or modifies the matrix of learning coefficients 18 By including the learning method 150 as an integral part of the expert system, the system can dynamically improve its matrix of learning coefficients as new examples or rules are fed into the system. Thus, in actual operation, anytime the actual correct responses are provided to the expert system, a new example is created which can be used in the learning method to update and improve the matrix of learning coefficients 18. The learning method 150 is also used to initially generate the matrix 18 from training examples and dependency lists. Rules may also be provided for use in determining or modifying the matrix of learning coefficients. Any known learning method may be used for the learning method 150. Herein, I describe a learning method of my own invention.

Figure 6A:
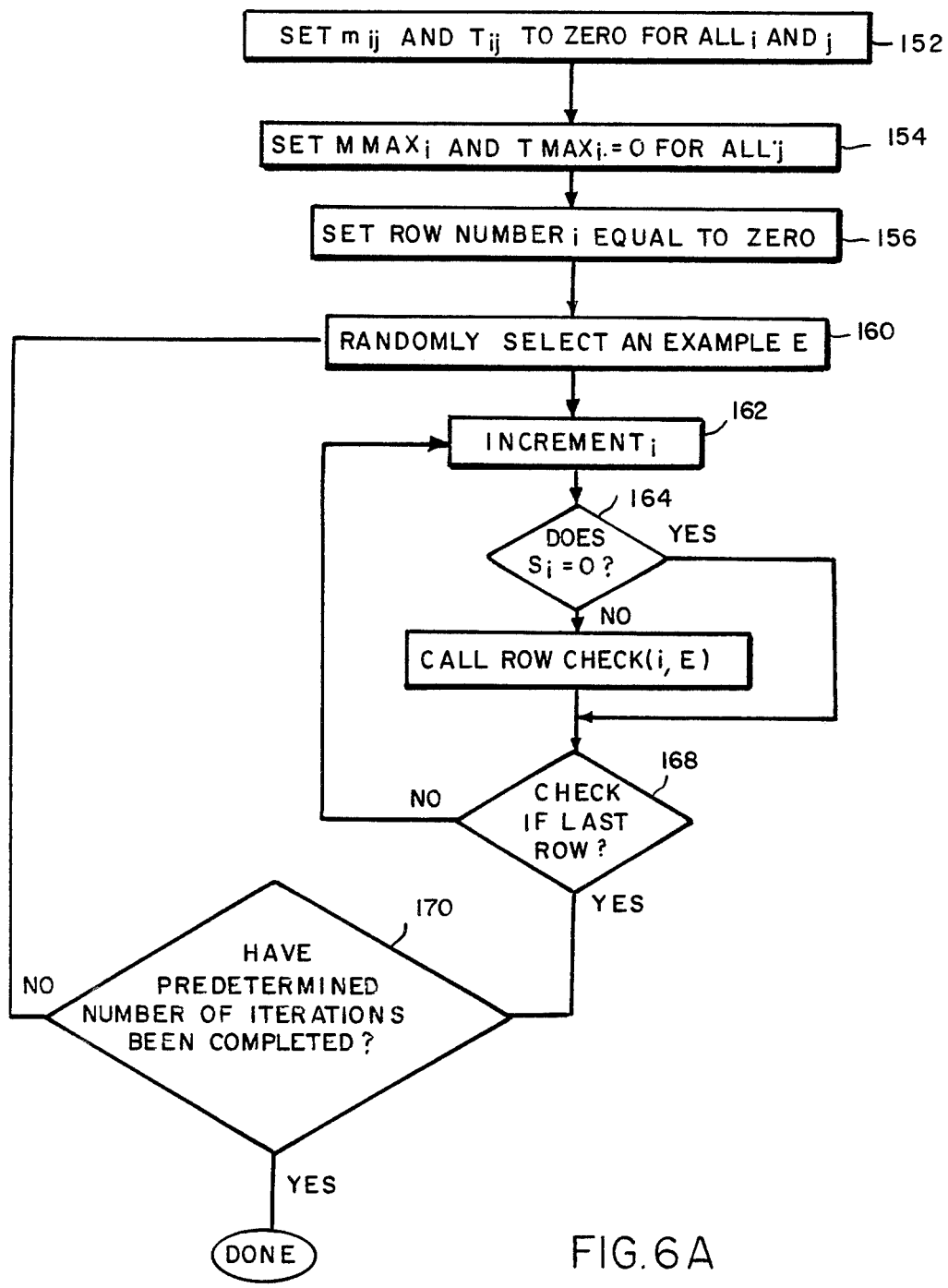
FIG. 6a is a flow chart of the learning method of the present invention.
Figure 6B:
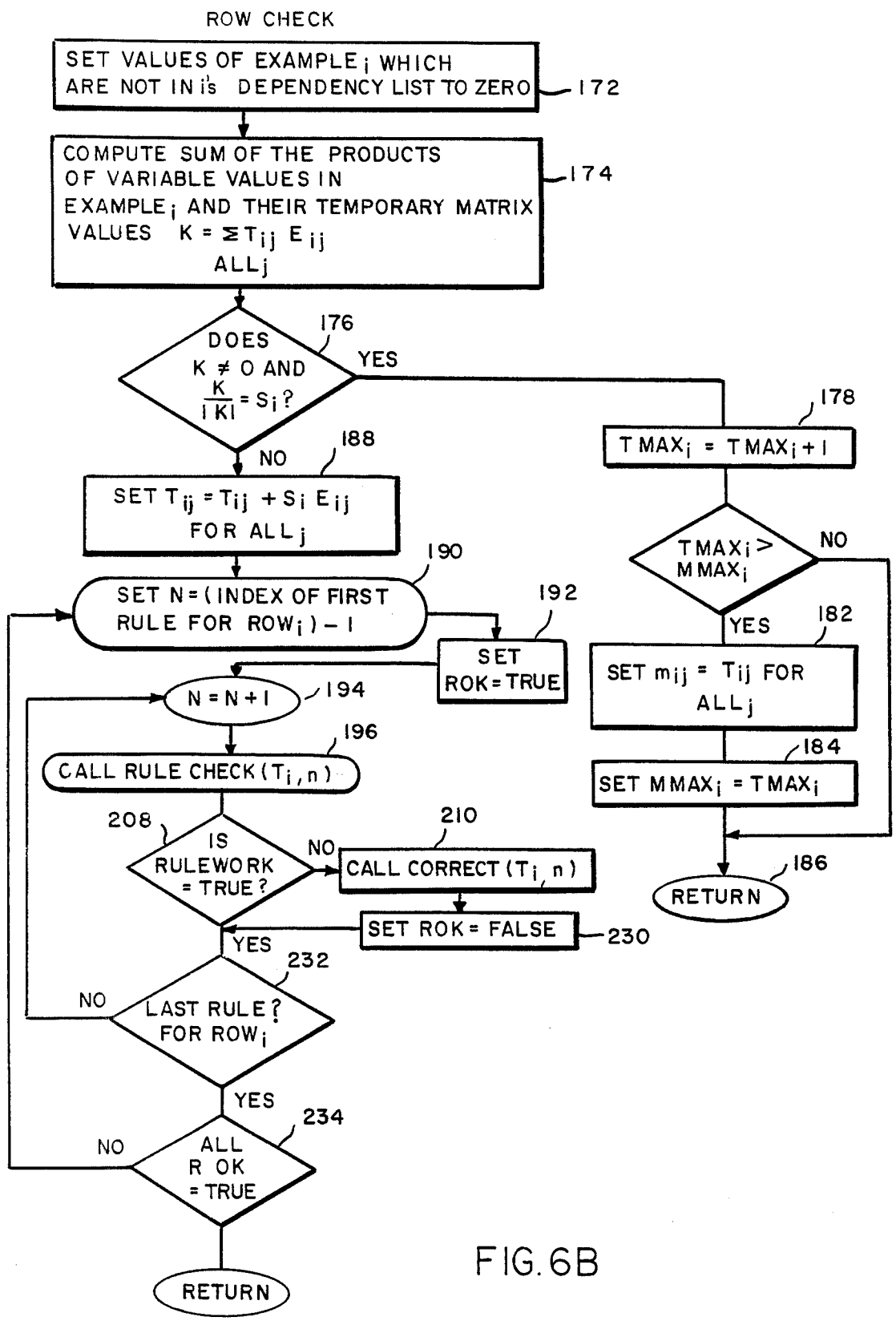

Referring now to FIGS. 6a, b, c and d, the learning method of my invention is illustrated. If the learning method is generating a matrix of learning coefficients 18 from scratch, it will be provided with a set of training examples. A set of rules may also be provided to contribute to the development of the matrix. In addition, it is helpful to provide a dependency list for each resultant variable. In the embodiment described herein, all rules for this system are stored on one large stack but are arranged so that rules which relate to a particular resultant variable are adjacent to one another on the stack.

The learning method begins by initializing its matrix. The learning method also prepares a temporary matrix identified in the flow charts as T, the learning method 150 continually refines the temporary matrix until it has determined that the values in same row of the temporary matrix probably produce better results than the values in the corresponding row of the present matrix. Thus, as examples are dynamically added to the system the learning method 150 will make changes to improve the matrix when appropriate.

In block 152, the learning method sets all values of the matrix and the temporary matrix to zero. In block 152 Mmax and Tmax for each row is set to zero. The Mmax and Tmax figures keep a record of how often the matrix row produces the correct results for an example or a rule as various examples and rules are tested on the matrix. Block 156 initializes i the index of the resultant variables which each have a matrix row. One of the training examples is randomly selected by block 160. Methods of random selection are well known in the art. A fixed entry of 1 is joined to the training example as its constant term in the 0th coordinate The learning method which is going to be described herein must be iterated a large number of times far exceeding the number of training examples. It has been shown that by using random selection of training examples in a large number of iterations that the values being determined for the matrix will converge on appropriate values for the data provided by the training examples. Inconsistencies in the rules, however, may prevent such a convergence.

Example E provides a value for each variable. If the value of a variable is not known, it is given the value zero. In the flow chart, the primary variable values are referenced by the variable j. The value of the resultant variable is referenced in the flow chart as $S_i$.

In block 162, index variable i is incremented. The learning method of the present invention generates the matrix for one resultant variable, in other words one matrix row at a time. In block 164, the learning method checks to see if the value of the resultant variable for the matrix row being generated is zero in the example. If the value is zero, then the example has no known effect on the value of the resultant variable and this particular example will not be useful in generating a matrix row for that resultant variable. Thus, the learning method will move on to the next row. If the resultant variable does have a given value for the example, the learning method will call ROW CHECK which is the learning program for refining the temporary matrix and determining whether the temporary matrix works better than the present matrix. In the dynamically operating expert system, although it is possible to reuse training examples to improve the matrix, it is not necessary. Dynamically, the expert system would call ROW CHECK for each row in the matrix for a new example as the example is received. Block 168, makes sure that each row has been checked by the learning method for the given example. After the learning method has completed work on one example, it checks in block 70 to determine whether it has completed the predetermined number of iterations. If it hasn't, it will return to randomly selecting a new example. If the predetermined number of iterations have been accomplished then the method is completed. Rather than predetermining the number of iterations, it may be desirable to provide a method of checking whether the matrix values are converging and whether they have reached a steady state.

ROW CHECK takes the example and creates a row of values $E_i$ in which the values of variables which are not in the dependency list of the resultant variable whose row is being worked on are set to zero. The other variables which will be either $+1$, 0 or $-1$ are left in $E_i$. In the presently described embodiment $+1$ corresponds to true, $-1$ corresponds to false and 0 corresponds to unknown. The result produced by this example for the resultant variable is referred to as $S_i$ and will either be true, $+1$, or false, $-1$.

In block 174 the method computes the sum of the products of the variable values in $E_i$ and their temporary matrix values. Then, in block 176, the method determines whether the sign of the sum is the same as the sign of the value for the resultant variable produced by the example. If the sum computed in block 174 has the same sign as the resultant variable, then the correct answer has been determined by the temporary matrix. Block 176 also makes sure that K does not equal zero since 0 would be an incorrect sum. If the temporary matrix produced the correct answer then Tmax is incremented by one in block 178. Tmax is compared to Mmax in block 180. Mmax is the number of times that the present matrix produced correct responses before it was allowed to take over as the matrix row. If Tmax is less that Mmax, then the preesnt matrix row will be retained and control returned to the point where row check was called from. If Tmax exceeds Mmax, then in block 182, the matrix is replaced by the temporary matrix for the row which has just been examined. In block 184, Mmax is now set equal to the value determined for Tmax. Then block 186 returns control to the point from which ROW CHECK was called.

If the temporary matrix produced the wrong result for the example being looked at, then in block 188 the temporary matrix row will be changed by adding to each value the product of $S_i$ the value of the resultant variable, times the value of each variable in $E_i$. Variables which are not on the dependency list have an E value equal to zero as set previously. After the new temporary matrix row has been created, it must be checked to make sure that it works for all rules which have been input into the system relating to the resultant variable whose row is being created.

In the flow chart the variable N is the index for the stack of rules. In block 190, N is set to one less than the first rule which is provided for the resultant variable whose row is i and is being created. In block 192, the flag ROK is set to true. In block 194 the index variable N is incremented to access the next rule which is provided for the row i which is being examined. Next, the temporary matrix row is checked to see if it works for the rule. The procedure RULE CHECK is called.

Figure 6C:
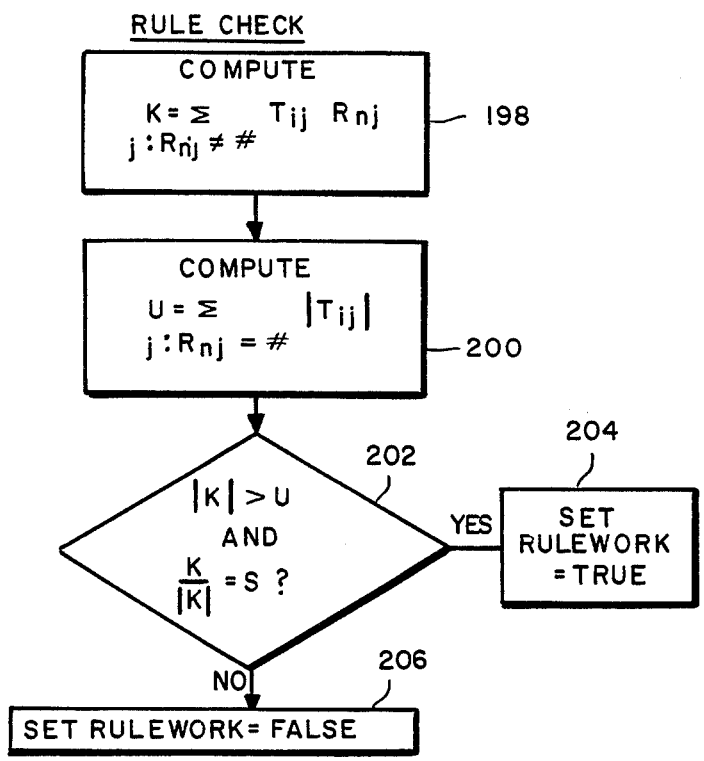
FIG. 6c is a flow chart of the routine RULECHECK called by the flow chart of FIG. 6b.
Figure 6D:
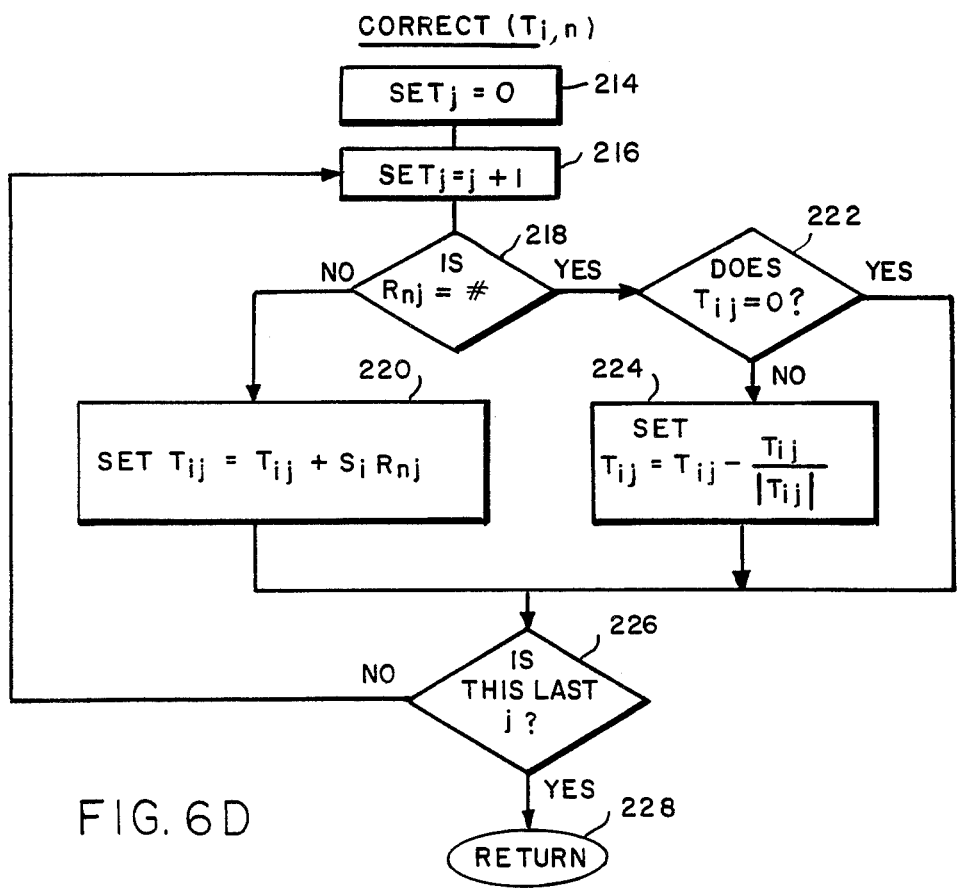
FIG. 6d is a flow chart of the routine CORRECT called by the flow chart of FIG. 6b.

Referring now to FIG. 6c, a rule gives a number of values for each primary variable on the depndncy list of the resultant variable. If a particular primary variable is not relevant to the rule, the rule will give it a value of #. The rule is of the form that if the variables have the values stated then the resultant variable will have the value S. Therefore, to determine whether the temporary matrix works in accordance with the rule, in block 198 the sum of the products of the temporary matrix T and the rule variables which are not provided with a hash mark is computed. In other words, all of the relevant variables in the rule are multiplied by their values in the temporary matrix and this is summed to give a value K. In the figure, Rn identifies the rule and j indexes through the primary variables. In block 200, U is computed as the sum of the absolute values of the temporary matrix values for the variables which are not relevant to the rule. Since these values are supposed to be not relevant, the absolute value of K should exceed the value U. If this is true, and if the sign of K is equal to the sign of S as desired by the rule, then the flag rulework is set to true. If the rule did not work, then in block 206, the flag rulework will be set to false.

Returning now to FIG. 6b, learning method asks if the rule worked in block 208. If the rule did not work, then the temporary matrix must be corrected. The program correct is called.

The routine CORRECT will index through the entire matrix row. In block 212 the index j is set to zero and in block 214 the index j is incremented. As the learning method moves across the row, the values of the rule are checked to see if they are irrelevant or not in block 218. If the variable is relevant, it will not be equal to a hash mark and block 220 will adjust the value of the temporary matrix by changing the value of the temporary matrix by adding to it the product of the value of the variable in the rule times the value S of the resultant variable as produced by the rule. If the variable is not relevant in the rule, then block 220 asks if the temporary matrix equals zero, if it does then there is no change. If the temporary matrix value is not equal to zero, then in block 224 the matrix value will be adjusted by subtracting the number defined by the present temporary matrix value divided by the absolute value of the temporary matrix value. In other words, the absolute value of the temporary matrix value will be reduced by one in block 224. After the adjustment has been made, block 226 checks to see if this is the last variable in the row, if it is not, the method will recycle until the row is completed. If it is the last variable, then control returns to the point from which correct was called.

Since the rule did not work first time through in block 230 ROK is set to false. The adjusted temporary matrix row will have to be rechecked. In block 232, the program asks whether it has checked all of the rules which apply to the row i which is being worked on. If not, the learning method will continue to cycle through its rule checking sequence. After all of the rules for a particular row have been checked, block 234 is provided to look at the flag ROK. If ROK is true, that means that the new temporaray matrix that has been set up for that particular row has worked for all of its rules. Thus, a new candidate matrix row has been created which will attempt to correctly produce the proper resultant variable value for examples as they are tested on the temporary matrix by the learning method. This temporary matrix row will remain the candidate until it produces a wrong answer or until its Tmax exceeds that of the present matrix row. If in block 234 it is determined that ROK is false, that means that the original temporary matrix row has been changed by the routine CORRECT and it did not work for all of the rules. Thus, this adjusted temporary matrix row which was adjusted at least once and possibly more will have to be cycled through all of the rules to see if it works on all of them. If the rules which are input into the system are inconsistent the learning method would be unable to arrive at a working temporary matrix row since none exist. In that event the rules would have to be debugged.

The learning method, as described, may advantageously be used to generate the matrix of learning coefficients 18 from a set of examples. Providing a set of rules and dependency lists is useful in quickly arriving at an effective matrix but they are not required. The general purpose expert system of the present invention may be used in a wide variety of applications. To change the application of the system it is only necessary to change the external interface and to assign variable names in generating a matrix.

Of course, it should be understood that various changes and modifications to the preferred embodiments described above will be apparent to those skilled in the art. For example, the specific algorithms identified for the inference engine may be changed to other algorithms which perform the same function to produce similar results. The learning method may also be changed yet still produce a matrix from a set of examples. As previously mentioned, a cost factor may be included for each input variable to provide a further basis on which to select what question will be asked. These and other changes can be made without departing from the spirit and the scope of the invention and without diminishing its attendant advantages. It is therefore intended that such changes and modifications be covered by the following claims.

I claim:

1. An expert system for providing responses, actions or inquires in response to a set of conditions comprising:
   a set of goal variables representative of said responses and said actions;
   a set of variables representative of said conditions;
   a matrix of learning coefficients providing a matrix value for each combination of one from a set of resultant variables and one from a set of primary variables, said set of resultant variables at least including a set of goal variables representative of said responses and said actions and said set of primary variables at least including a set of varaibles representative of said conditions;
   an external interface for receiving said conditions to establish known primary variables and outputting said responses, actions or inquiries; and
   an inference engine including:
   means for computing likely values of said resultant variables from known primary variables in accordance with said matrix of learning coefficients,
   means for determining whether said likely value is a final determination, said likely value being a final determination when said likely value would be unchanged regardless of the value of the primary variables whose values are not known;
   means for determining a useful condition which will contribute to making a final determination of a resultant variable whose value has not been finally determined; and
   means for causing said external interface to output responses or actions in accordance with the finally determine values of said goal variables and to output an inquiry making for said useful condition.

2. The expert system of claim 1 wherein a goal variable may also be a primary variable.

3. The expert system of claim 1 wherein said matrix of learning coefficients can be generated with examples including values for said conditions with the corresponding responses or actions which should be produced in response to said condition values.

4. The expert system of claim 1 further comprising a learning method for generating said matrix of learning coefficients from examples including values for said conditions with the corresponding responses or actions which should be produced in response to said condition values.

5. The expert system of claim 4 wherein said learning method is also used for modifying said matrix of learning coefficients in response to examples including values for said conditions with the corresponding responses or actions which should be produced in response to said condition values.

6. The expert system of claim 4 wherein said learning method generates a matrix of learning coefficients which properly computes the values of resultant variables for as many of the examples provided to it as is possible.

7. The expert system of claim 1 further comprising learning method which uses rules that must be satisfied for the resultant variables to which it applies, for generating said matrix of learning coefficients.

8. The expert system of claim 7 further comprising a rule compiler for translating rules which are input through said external interface into rules having a matrix form for use in said learning method.

9. The expert system of claim 1 wherein said primary variables may take on integer or fractional values without restriction to the interval from $-1$ to $+1$ and wherein the value of a resultant variable depends on the sign of its arithmetically computed value.

10. The expert system of claim 1 wherein said matrix of coefficients has exactly one resultant variable.

11. A method for generating and operating an expert system comprising the steps of:
   inputting into said expert system a set of training examples each including values for a plurality of conditions with corresponding values for the responses or actions which should be produced in response to said condition values;
   generating a matrix of learning coefficients within said expert system corresponding to said set of training examples, said matrix of learning coefficients having a matrix value for each combination of one from a set of resultant variables and one from a set of primary variables, said set of resultant variables at least including a set of variables corresponding to said responses and said actions and said set of primary variables at least including a set of variables representative of said conditions;
   inputting known values for a set of conditions into said expert system; and
   determining the value of a resultant variable by combining said known values for a set of conditions with the matrix values associated with said resultant variable; and
   outputting responses or actions depending on the value of the corresponding resultant variable.

12. The method of claim 11 further comprising determining a useful condition whose value is unknown and requesting the value of said useful condition.

13. The method of claim 11 wherein said step of determining the value of a resultant variable is performed by summing the products formed by multiplying each of said known values by the matrix value in the matrix of learning coefficients associated with both said resultant variable and the condition corresponding to the known value.

14. The method of claim 13 further comprising determining a likelihood for a particular response or action by comparing the sum of the products of the values representative of said known conditions and the matrix values associated with both said known conditions and said particular response or action with the largest possible value of the sum of these same products computed for conditions which are not known.

15. The method of claim 13 further comprising determining a likelihood for a particular response or action by comparing the sum of the products of the likelihoods of the primary variables and the matrix value corresponding to said particular response or action in said matrix of learning coefficients to sum of the absolute values of the matrix values corresponding to said particular response or action.

16. The method of claim 11 further comprising the step of inputting a set of rules and wherein said matrix of learning coefficients is generated so that it satisfies said set of rules.

17. The method of claim 11 wherein said step of generating a matrix of learning coefficients comprises the steps of:
   (a) randomly selecting one of said training examples:
   (b) testing, for each resultant variable which is provided a value in said training example, matrix values in a temporary matrix of learning coefficients associated with said resultant variable to determine whether the matrix values combine with the variable values of the example to determine the proper response for the resultant variable as provided by the training example;
   (c) replacing the matrix values associated with a resultant variable in said matrix of learning coefficients with the matrix values for said resultant variable from said temporary matrix of learning coefficients when said temporary matrix values have determined the correct response for a greater number of training examples than had been determined by the original matrix of learning coefficients;
   (d) modifying the matrix values associated with a resultant variable in the temporary matrix of learning coefficients when said matrix values determine an incorrect response for the training example; and
   (e) repeating steps a-d at least a predetermined number of times.

18. The method of claim 17 wherein step b is performed by computing the sum of the products of the variable values in said examples and their associated temporary matrix values.

19. The method of claim 17 wherein said learning method further comprises counting the number of consecutive times the temporary matrix values associated with each resultant variable arise at the correct response for the resultant variable as provided by an example.

20. The method of claim 17 wherein said step of modifying the temporary matrix comprises for each matrix value associated with a resultant variable adding to the matrix value the product of the value in the example of the resultant variable and the value in the example of the primary variable associated with the matrix value.

21. The method of claim 17 wherein said learning method further comprises the step of checking to determine whether the modified temporary matrix values associated with a resultant variable satisfy the requirements of each rule corresponding to that resultant variable.

22. The method of claim 21 wherein checking to determine whether the requirements of a rule are satisfied includes comparing the sum of the products of the modified temporary matrix values and their associated values in the rule with the sum of the modified temporary matrix values associated with each of the primary variables which are irrelevant to the rule.

23. The method of claim 21 wherein said learning method further comprises modifying the temporary matrix values associated with the resultant variable if they do not satisfy the requirements of a rule, said modification including reducing the absolute value of the modified temporary matrix values associated with primary variables which are irrelevant to the rule and adding to the remaining temporary matrix values the product of the corresponding value in the rule and the value of the resultant variable as determined by the rule.

24. An inference engine for use in an expert system controlled by a matrix of learning coefficients having a matrix value for each combination of one from a set of resultant variables and one from a set of primary variables, said set of primary variables at least including a set of input variables, said inference engine comprising:
   means for calculating a likely value of a resultant variable from known values of primary variables and the matrix values associated with said resultant variable;
   means for determining whether said likely value is a final determination, said likely value being a final determination when said likely value would be unchanged regardless of the value of the primary variables whose values are not known; and
   means for determinig an input variable which will contribute to making a final determination of a resultant variable whose value has not been finally determined.

25. The matrix controlled inference engine of claim 24 wherein each input variable is assigned a cost number roughly corresponding to how costly it would be to obtain the value of the variable and wherein said cost number is considered by said means for determining an input variable which will contribute to making a final determination of a resultant variable.

26. The matrix controlled inference engine of claim 24 wherein said means for determining whether said likely value is a final determination comprises comparing the sum of the products of the known primary variable values and their associated matrix values with the sum of the absolute values of the matrix values of the primary variables which are not known.

27. The inference engine of claim 24 wherein said means for calculating a likely value of a resultant variable is performed by summing the products formed by multiplying each of said known values of primary variables by the matrix value in the matrix of learning coefficients associated with both said resultant variable and the primary variable corresponding to the known value.

28. A learning process for operating a general purpose computer having a knowledge base including a matrix of learning coefficients, which includes a matrix value for each combination of one of a set of resultant variables and one of a set of primary variables, to enhance said matrix, comprising the steps of:
   (a) inputting a set of examples, each example including values for at least one primary variable and values for at least one resultant variable;
   (b) randomly selecting one of said examples;
   (c) testing, for each resultant variable which is provided a value in said example, matrix values in a temporary matrix of learning coefficients associated with said resultant variable to determine whether the matrix values combine with the primary variable values of the example to determine the proper value of said resultant variable as provided by the example;
   (d) replacing the matrix values associated with a resultant variable in said matrix of learning coefficients with the matrix values for said resultant variable from said temporary matrix of learning coefficients when said temporary matrix values have determined the correct value for said resultant variable for a greater number of examples than had been correctly determined by the present matrix of learning coefficients;
   (e) modifying the temporary matrix values associated with a resultant variable in the temporary matrix of learning coefficients when said temporary matrix values determine an incorrect response for the examples; and
   (f) repeating steps b–e at least a predetermined number of times.

29. The learning process of claim 28 wherein step c is performed by computing the sum of the products of the primary variable values in said example and their associated temporary matrix values.

30. The learning process of claim 28 further comprising the step of counting the number of consecutive times the temporary matrix values associated with each resultant variable determine the correct response for the resultant variable as provided by an example.

31. The learning process of claim 28 wherein said step of modifying the temporary matrix comprises for each temporary matrix value associated with a resultant variable adding to the temporary matrix values the product of the value in the example of the resultant variable and the value in the example of the primary variable associated with the temporary matrix value.

32. The learning process of claim 28 further comprising the steps of inputting a set of rules and checking to determine whether the modified temporary matrix values associated with a resultant variable satisfy the requirements of each rule corresponding to said resultant variable.

33. The learning process of claim 32 wherein checking to determine whether the requirements of a rule are satisfied includes comparing the sum of the products of the modified temporary matrix values and their associated values in the rule with the sum of the modified temporary matrix values associated with each of the primary variables which are irrelevant to the rule.

34. The learning process of claim 32 further comprising the step of modifying the temporary matrix values associated with said resultant variable if they do not satisfy the requirements of a rule, said step of modifying including reducing the absolute value of the modified temporary matrix values associated with primary variables which are irrelevant to the rule and adding to the remaining temporary matrix values the product of the corresponding value in the rule and the value of the resultant variable as determined by the rule.

35. A learning process for operating a general purpose computer having a knowledge base, including a matrix of learning coefficients which includes a matrix value for each combination of one of a set of resultant variables and one of a set of primary variables to enhance said matrix comprising the steps of:
   (a) providing an example including values for at least one primary variable and values for at least one resultant variable;
   (b) testing, for each resultant variable which is provided a value in said example, matrix values in a temporary matrix of learning coefficients associated with said resultant variable to determine whether the matrix values combine with the primary variable values of the example to determine the proper value of said resultant variable as provided by the example;

(c) replacing the matrix values associated with a resultant variable in said matrix of learning coefficients with the matrix values for said resultant variable from said temporary matrix of learning coefficients when said temporary matrix values have determined the correct value for said resultant variable for a greater number of examples than had been correctly determined by the present matrix of learning coefficients;

(d) modifying the temporary matrix values associated with a resultant variable in the temporary matrix of learning coefficients when said temporary matrix values determine an incorrect response for the example; and (e) repeating steps b-d at least a predetermined number of times.

36. The learning process of claim 35 wherein step b is performed by computing the sum of the products of the primary variable values in said example and their associated temporary matrix values.

* * * * *

UNITED STATES PATENT AND TRADEMARK OFFICE
CERTIFICATE OF CORRECTION

PATENT NO. : 4,730,259

DATED : March 8, 1988

INVENTOR(S) : Stephen I. Gallant

It is certified that error appears in the above—identified patent and that said Letters Patent is hereby corrected as shown below:

Column 1, line 59, please delete "prope" and insert --proper--.
Column 2, line 8, please delete "a" and insert --an--.
Column 7, line 37, please delete "a" and insert --at--.
Column 8, line 52, please delete "variatbles" and insert --variables--.
Column 16, line 55, please delete "making" and insert --asking--.
Column 18, line 43, please delete "examples" and insert --example--.

Signed and Sealed this

Fifteenth Day of November, 1988

Attest:

DONALD J. QUIGG

Attesting Officer

Commissioner of Patents and Trademarks